United States Patent
Sterkers et al.

(10) Patent No.: US 10,524,960 B2
(45) Date of Patent: Jan. 7, 2020

(54) OTOLOGIC SURGERY DEVICE AND METHOD FOR DRILLING A PASSAGE UP TO A COCHLEA

(71) Applicant: COLLIN, Bagneux (FR)

(72) Inventors: Olivier Sterkers, Paris (FR); Alexis Bozorg Grayeli, Paris (FR); Mathieu Miroir, Massy (FR); Yann Nguyen, Paris (FR)

(73) Assignee: COLLIN, Bagneux (FR)

( * ) Notice: Subject to any disclaimer, the term of this patent is extended or adjusted under 35 U.S.C. 154(b) by 944 days.

(21) Appl. No.: 13/899,254

(22) Filed: May 21, 2013

(65) Prior Publication Data
US 2013/0317517 A1    Nov. 28, 2013

(30) Foreign Application Priority Data
May 23, 2012    (FR) ..................................... 12 54730

(51) Int. Cl.
| | |
|---|---|
| *A61B 34/30* | (2016.01) |
| *A61F 11/00* | (2006.01) |
| *A61B 17/34* | (2006.01) |
| *A61B 17/17* | (2006.01) |
| *A61N 1/05* | (2006.01) |
| *A61B 90/00* | (2016.01) |
| *A61B 34/10* | (2016.01) |

(52) U.S. Cl.
CPC ........ *A61F 11/004* (2013.01); *A61B 17/3468* (2013.01); *A61B 34/30* (2016.02); *A61B 17/1771* (2016.11); *A61B 2034/107* (2016.02); *A61B 2090/065* (2016.02); *A61N 1/0541* (2013.01)

(58) Field of Classification Search
CPC ................. A61F 11/004; A61N 1/0541; A61B 2017/1771; A61B 17/3468; A61B 17/1615; A61B 17/1679; A61B 34/30; A61B 17/1771
USPC .......................... 606/79, 80; 623/10; 600/379
See application file for complete search history.

(56) References Cited

U.S. PATENT DOCUMENTS

| | | | | |
|---|---|---|---|---|
| 6,228,089 | B1* | 5/2001 | Wahrburg | A61B 17/1668 606/130 |
| 2006/0247517 | A1* | 11/2006 | Labadie | A61B 5/06 600/426 |
| 2010/0114288 | A1 | 5/2010 | Haller et al. | |
| 2011/0319913 | A1 | 12/2011 | Labadie et al. | |

(Continued)

OTHER PUBLICATIONS

French Search Report for FR 1254730 dated Feb. 7, 2013.

*Primary Examiner* — Si Ming Ku
(74) *Attorney, Agent, or Firm* — Sughrue Mion, PLLC

(57) ABSTRACT

A device for providing assistance in otologic surgery of a patient who is to be implanted with a cochlea implant. The device includes a mechanism for identifying the positions of an entry point (21) on the surface of the cochlea and of a control point (20) in the sinus tympani, and operable via the external auditory canal; a processor (100) to respond to the coordinates of the points to determine a straight-line path (T) passing through the two points and defining a docking point (22) on the outside surface of the mastoid bone; and a drilling mechanism (25, 27) for drilling a passage up to the cochlea through the mastoid bone along the straight-line path, so as to create a passage up to the cochlea.

14 Claims, 2 Drawing Sheets

(56) References Cited

U.S. PATENT DOCUMENTS

2012/0059378 A1* 3/2012 Farrell ............... A61B 17/1626
606/80

* cited by examiner

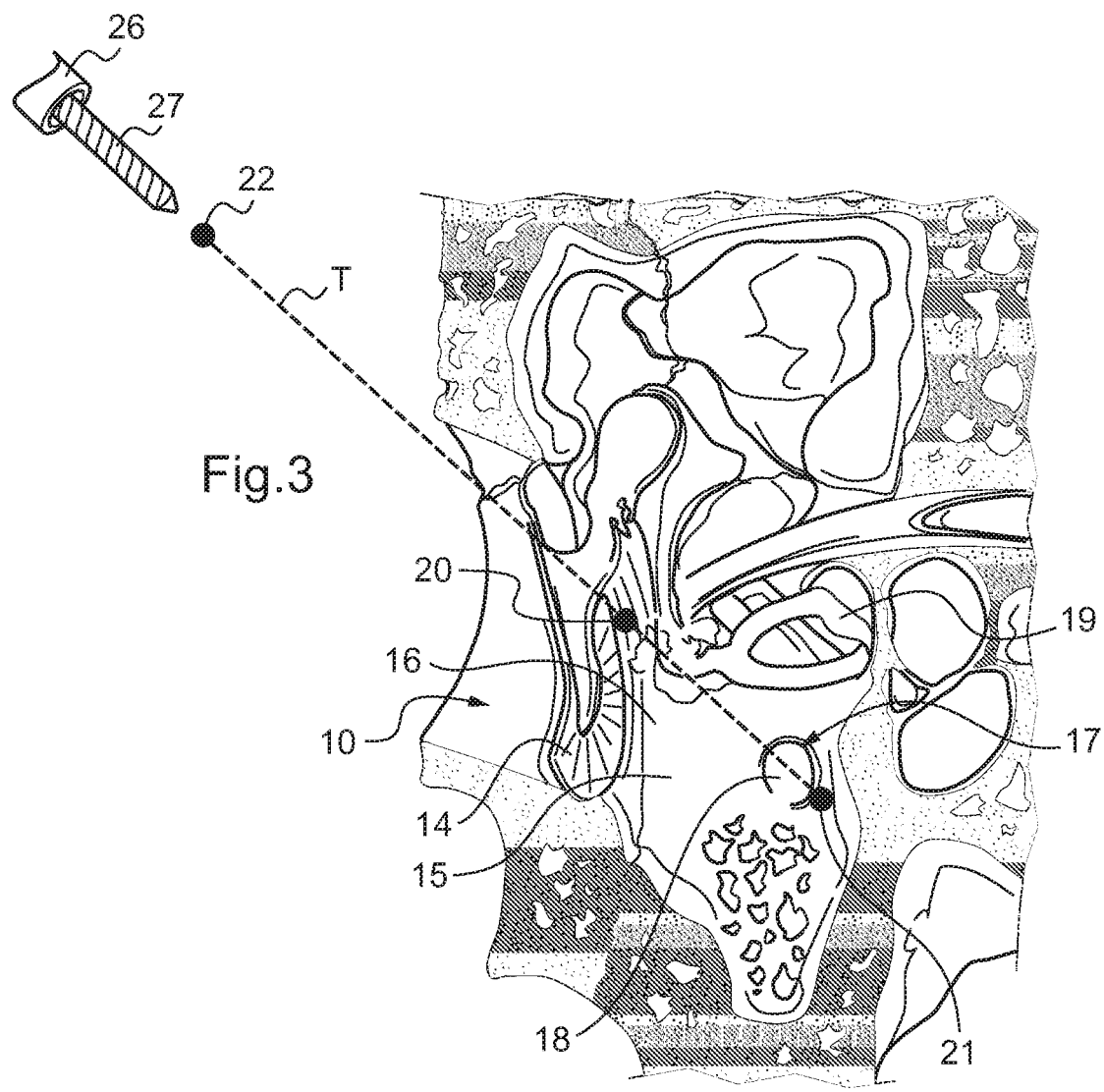

OTOLOGIC SURGERY DEVICE AND METHOD FOR DRILLING A PASSAGE UP TO A COCHLEA

The invention relates to a device for providing assistance to otologic surgery of a patient who is to be implanted with a cochlea implant.

TECHNOLOGICAL BACKGROUND OF THE INVENTION

Total or partial deafnesses are now being treated by putting a cochlea implant into place in the cochlea, and more precisely an electrode carrier carrying an array of electrodes and connected to a receiver/stimulator that is implanted in the patient's skull.

The conventional technique for implanting a cochlea consists in performing mastoidectomy by removing the mastoid bone that projects behind the pinna. Then a narrow passage between the facial nerve and the external auditory canal is provided by means of a posterior tympanotomy. Finally, a cochleostomy gives access to the inside of the cochlea in order to enable the electrode carrier to be put into place in the cochlea. That technique is considered as being very invasive.

Recent proposals have been made to perform such operations with the help of a surgical assistance robot, the robot being guided by means of navigation algorithms based on preoperative or peroperative images, e.g. obtained with a scanner. In particular, the robot has an arm, the end of which is provided with a drilling tool (such as a drill bit) for drilling an access passage to the entry of the cochlea through the mastoid bone. Such techniques are considerably less invasive.

Nevertheless, the accuracy of such navigation (which accuracy is of millimeter order) is not good enough to be sure of making a passage through the mastoid bone without running the risk of injuring the facial nerve. This nerve is situated on the approach path for posterior tympanotomy.

OBJECT OF THE INVENTION

An object of the invention is to provide a device for providing assistance in otological surgery of a patient who is to be implanted with a cochlea implant, which device makes it possible to determine an access path to the entry of a cochlea such that if it is followed by a drilling tool ought to provide access to the entry of the cochlea while avoiding any lesion to the facial nerve.

BRIEF DESCRIPTION OF THE INVENTION

In order to achieve this object, the invention provides a device for providing assistance in otologic surgery of a patient who is to be implanted with a cochlea implant, the device comprising:
  means for identifying the positions of an entry point on the surface of the cochlea and of a control point in the sinus tympani, these means being operable via the external auditory canal;
  processor means to respond to the coordinates of said points to determine a straight-line path passing through those two points and defining a docking point on the outside surface of the mastoid bone; and
  means for making a passage up to the cochlea through the mastoid bone along said straight-line path.

In a particular implementation of the invention, the positions of the points are identified by means of a feeler mounted at the end of a robot arm. The practitioner brings the feeler into contact with the looked-for points and the coordinates of those points are taken merely by reading the signals from the position sensors of the arm. A high degree of accuracy can commonly be achieved with the robot arms that have already been developed.

The identified point forming the entry point into the cochlea preferably lies on the anterior lower border of the round window of the cochlea. Also preferably, the identified point forming the control point in the sinus tympani is situated behind the rim of the sulcus tympani.

These points make it possible to define a docking point on the mastoid, which docking point lies substantially in the cribriform zone of the mastoid, which is easily accessible for a drilling tool.

Various simulations have shown that by drilling the mastoid bone while scrupulously following the straight-line path as determined in this way, an access path is made up to the cochleostomy zone while avoiding the facial nerve. This makes it possible to provide access to the cochlea while minimizing invasive operations and avoiding injuring the facial nerve.

In a particular implementation of the invention, the drilling tool used for drilling the mastoid bone is also used for performing cochleostomy, in a single movement. The drilling is thus like making a tunnel providing direct access to the cochlea for treatment or fitting with an electrode carrier.

DESCRIPTION OF THE FIGURES

The invention can be better understood in the light of the following description of a particular embodiment of the invention, given with reference to the figures of the accompanying drawings, in which:
FIG. 3 is a section view of the patient's skull, also showing the identified points.

DETAILED DESCRIPTION OF AN EMBODIMENT OF THE INVENTION

Figure 1:
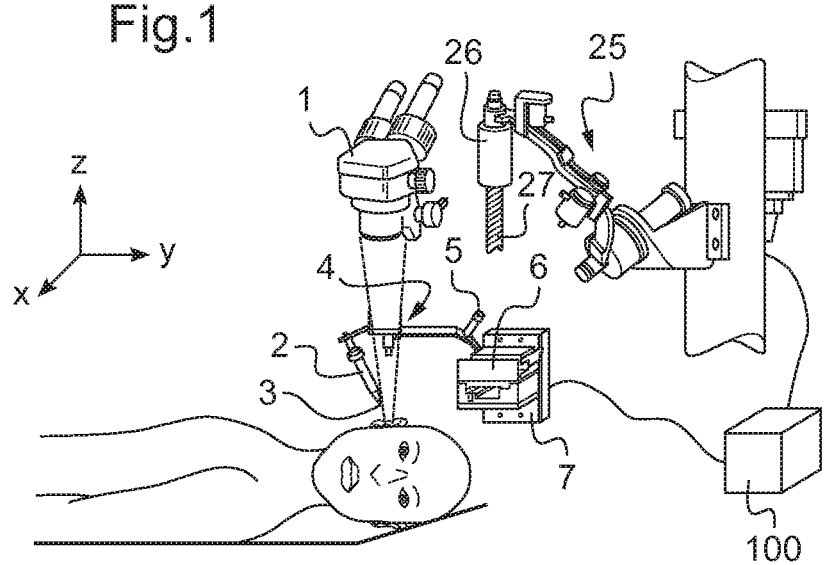
FIG. 1 is a diagrammatic view of a device for providing assistance in otologic surgery.

The invention seeks to provide access to the cochlea in mini-invasive manner, traumatizing the patient as little as possible. As can be seen in FIG. 1, the patient is in the prone position with the head held stationary on one side, so that the external auditory canal extends upwards. Means for holding the head stationary are well known and do not form part of the invention.

The practitioner has means for visually inspecting the external auditory canal, specifically an operating microscope 1 with its field of view marked with a dashed line. The practitioner also has a feeler 2 with a sensitive end 3. The feeler 2 is shown in this example as being at the distal end of a hinged arm 4 in which each of the hinges is provided with an angular position sensor 5 (only one of these sensors is referenced). The hinged arm 4 has a proximal end connected to a base 6 that is movably mounted on a support 7 to move along three axes in translation. Each axis is fitted with a corresponding position sensor. By using the signals from the position sensors, it is possible at all times to identify the position in three dimensions of the sensitive tip 3 of the feeler 2. In this example, the coordinates of the points as identified in this way are expressed in an absolute frame of reference R. The signals from the position sensors are collected by a processor unit 100 (e.g. a personal computer having an appropriate acquisition card) that is capable of calculating the coordinates of the points that have been felt as a function of the signals from the position sensors.

Figure 2:
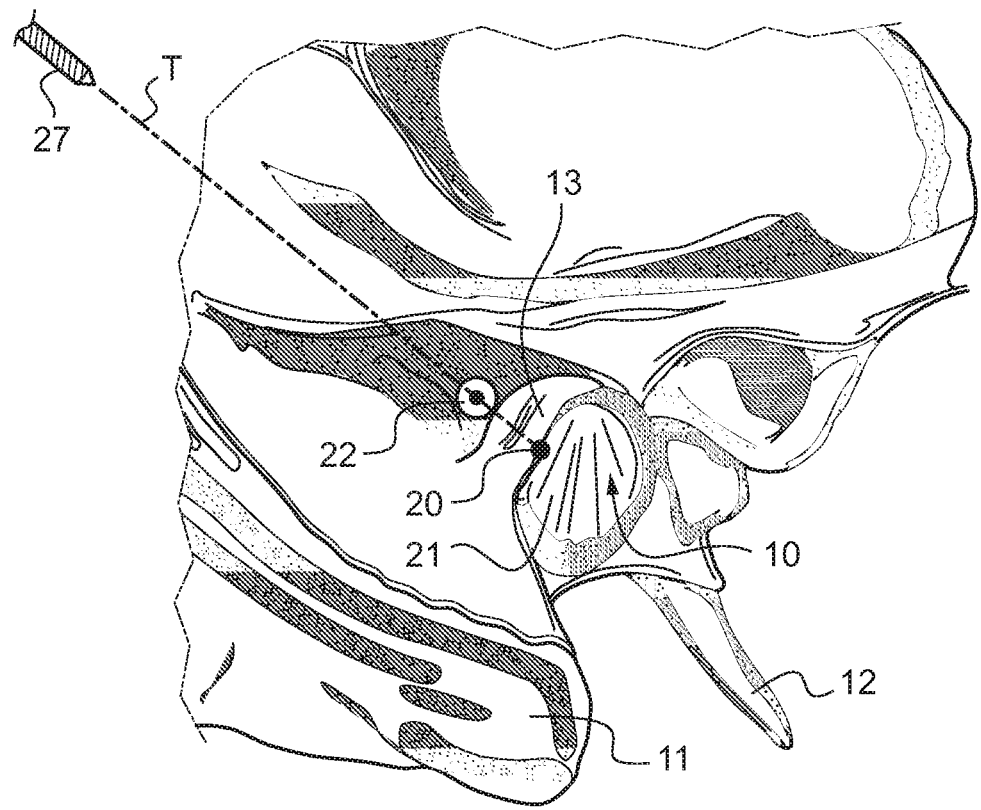
FIG. 2 is a fragmentary side view of a patient's skull, showing the identified points.

The way in which the feeler is used is described below with reference to FIG. 2, where there can be seen the portions of the skull surrounding the external auditory canal 10, and in particular the mastoid process 11, the styloid process 12, and Henle's suprameatal spine 13, and also with reference to FIG. 3, in which there can be seen the external auditory canal 10, the eardrum 14, the sinus tympani 15, the rim 16 of the tympanic sulcus, the round window 17 of the cochlea, and the lower anterior border 18 thereof, and finally the facial nerve 19, which can be seen passes close to the drilling zone.

After separating the skin from the external auditory canal and from the eardrum, and where necessary after performing tympanostomy, the practitioner inserts the feeler into the external auditory canal 10 and brings the sensitive tip 3 of the feeler 2 into the region of the sinus tympani, and more precisely to substantially one millimeter behind rim 16 of the tympanic sulcus. The practitioner presses on an acquisition button associated with the feeler 2 in order to measure and store in the processor unit 100 the coordinates of the point as felt in this way, which is referred to below as the control point 20.

Thereafter, the practitioner pushes the feeler 2 further forward in order to feel a point on the cochlea, situated more precisely on the lower anterior border 18 of the round window of the cochlea. In the same manner, the practitioner presses on an acquisition button associated with the feeler 2 in order to measure and store in the processor unit 100 the coordinates of the point as felt in this way, referred to herein as the entry point 21. The entry point 21 is substantially at the center of the cochleostomy that is to be performed.

In a variant implementation, the acquisition of these two points takes place the other way around, so that the control point 20 in the sinus tympani is felt before feeling the entry point 21 on the surface of the cochlea.

Furthermore, and in another variant implementation, feeling is assisted; for this purpose, if the articulated arm 4 is motor-driven, the feeler 2 is brought automatically to the proximity of the points that are to be felt by the processor unit 100 controlling the motors of the articulated arm so as to guide the feeler 2, e.g. on the basis of preoperative images of the external auditory canal. It then remains for the practitioner to feel very accurately the looked-for points by taking over and guiding the feeler, e.g. with the help of a joystick or any other control member.

In the invention, the processor unit 100 is programmed so that after acquiring the control point 20 and the entry point 21, it determines the equation for a straight-line path T passing those two points. It is along this path that the passage to the cochlea will be formed. The path T defines a point on the outside surface of the skull in the cribriform zone of the mastoid bone, which forms the docking point 22 for the tool with the mastoid bone.

For this purpose, the device of the invention has an articulated and motor-driven robot arm 25 that is provided at its distal end with a motor-driven spindle 26 carrying a drilling tool, specifically in this example a drill bit 27. The robot arm 25 is connected to the processor unit 100 so that it controls the robot arm 25 in order to align the axis of the drill bit 27 on the straight-line path T, so as to put into rotation, and then drill the mastoid bone along the straight-line path T.

The drill bit 27 then docks with the skull at the docking point 22, drills into the mastoid bone towards the control point 20, opens out into the external auditory canal, and continues along its path towards the entry point 21. In so doing, the drill bit 27 clears a passage up to the cochlea. By continuing forwards, the drill bit 27 forms a cochleostomy in the wall of the cochlea thus releasing a complete passage to the inside of the cochlea and making it possible to insert the electrode carrier of a cochlea implant therein.

The drilling operation is advantageously performed under visual monitoring by means of the operating microscope 1. Visual monitoring is advantageously associated with electromyogaphic monitoring of the facial nerve making it possible at all times to detect potential contact between the tool and the facial nerve, or to determine at all times the distance between the tip of the tool and the facial nerve, using a method that is itself known.

Naturally, the invention is not limited to the above description, but covers any variant coming within the ambit defined by the claims.

In particular, although in the implementation shown the feeler and the drilling tool are carried by distinct arms, they could be carried by the same arm, either simultaneously or sequentially. The arm is then preferably an arm that is articulated, motor-driven, and fitted with position sensors at each of its degrees of freedom. For example, it is possible to use an assisted surgery device known under the name Robotol, as described in "Robotol: from design to evaluation of the robot for middle ear surgery" M. Miroir, et al., published in Intelligent Robots and Systems, 2010, IEEE/RSJ International Conference.

Although in the example shown the means for identifying the entry and control points are constituted by a feeler, any other identification means could be used providing such identification means are operable in the external auditory canal, such as for example laser illumination of the points to be identified, with the light spot as created in this way being located with the help of a charge-coupled device (CCD) camera. It is also possible to use stereo viewing methods or electromagnetic identification methods in which a stylus carrying elements for determining its position in three dimensions is manipulated by the surgeon.

It is also possible to use position-identification methods in correlation with images previously obtained by a scanner or by magnetic resonant imaging (MRI).

Although in the implementation shown the same drilling tool is used both for performing mastoidostomy and cochleostomy, it would be possible to perform mastoidostomy with a first tool and then change the tool before performing cochleostomy.

The invention claimed is:

1. An otologic surgery device for providing assistance in otologic surgery of a patient who is to be implanted with a cochlea implant, the otologic surgery device comprising:
position-identification means for identifying coordinates of an entry point on a surface of a cochlea and of a control point in a sinus tympani, the position-identification means being operable via an external auditory canal, wherein the position-identification means is configured to acquire and store respective positions of points selected directly on the surface of the cochlea and in the sinus tympani and is adapted to be operated by a practitioner of the otologic surgery device prior to drilling to thereby allow the practitioner to selectively acquire and store each of the entry point and the control point;

processor means to respond to the coordinates of the entry point and the control point as identified by the position-identification means to determine an equation for a straight-line path passing through the entry point and the control point and defining a docking point on the straight-line path on an outside surface of a mastoid bone such that the docking point, the control point and the entry point are on the same straight-line path; and otologic drilling means, separate and distinct from the position-identification means, for drilling a passage from the docking point up to the cochlea through the mastoid bone along said straight-line path as determined by the equation, so as to create a passage up to the cochlea, wherein the docking point for the otologic drilling means and the straight-line path followed by the otologic drilling means are predetermined by the device before drilling the passage.

2. The otologic surgery device according to claim 1, wherein the position-identification means comprises a feeler having a sensitive tip configured to be brought into contact with the cochlea and with the sinus tympani via the external auditory canal in order to feel the entry point and the control point.

3. The otologic surgery device according to claim 2, wherein the feeler is mounted at an end of an articulated arm having position sensors associated with each degree of freedom of the arm, such that a position of the sensitive tip of the feeler can be deduced by a processor unit from signals generated by the position sensors.

4. The otologic surgery device according to claim 1, wherein the otologic drilling means comprises an articulated and motor-driven arm carrying an otologic drilling tool at an end of the arm, said arm being controllable to put the otologic drilling tool into alignment with said straight-line path and to move the otologic drilling tool therealong.

5. The otologic surgery device according to claim 3, wherein the otologic drilling means comprises an otologic drilling tool; wherein both the feeler and the otologic drilling tool are carried by the articulated arm that is controllable to put the otologic drilling tool into alignment with the straight-line path and to move the otologic drilling tool along the straight-line path; and wherein the articulated arm is motor-driven and provided with position sensors associated with each degree of freedom of the articulated arm.

6. The otologic surgery device according to claim 1, including optical monitoring means for monitoring the external auditory canal.

7. The otologic surgery device according to claim 1, including electromyographic means for monitoring a facial nerve.

8. A method of otologic surgery, the method comprising the steps of:
providing the otologic surgery device of claim 1;
operating the position-identification means to identify the coordinates of the entry point on the surface of the cochlea on passing via the external auditory canal;
operating the position-identification means to identify the coordinates of the control point in the sinus tympani on passing via the external auditory canal;
operating the processor means to determine, using the coordinates of the entry point and the control point as identified by the position-identification means, an equation for the straight-line path that passes through the entry point and the control point; and
operating the otologic drilling means to make a passage from the docking point up to the cochlea through the mastoid bone along said straight-line path as determined by the equation.

9. The method according to claim 8, wherein the otologic drilling means are operated so as to perform cochleostomy in line with the passage through the mastoid bone along said straight-line path.

10. The method according to claim 8, wherein the entry point is determined by identifying the position of a point on an anterior lower border of a round window of the cochlea.

11. The method according to claim 8, wherein the control point is determined by identifying the position of a point behind a rim of a tympanic sulcus.

12. An otologic surgery device for providing assistance in otologic surgery of a patient who is to be implanted with a cochlea implant, the otologic surgery device comprising:
a feeler mechanism having a sensitive tip configured to identify coordinates of an entry point on a surface of a cochlea and of a control point in a sinus tympani, the feeler mechanism being operable via an external auditory canal, wherein the feeler mechanism is configured to acquire and store respective positions of points selected directly on the surface of the cochlea and in the sinus tympani and is adapted to be operated by a practitioner of the otologic surgery device prior to drilling to thereby allow the practitioner to selectively acquire and store each of the entry point and the control point;
a processor unit programmed to respond to the coordinates of the entry point and the control point as identified by the feeler mechanism to determine an equation for a straight-line path passing through the entry point and the control point and defining a docking point on the straight-line path on an outside surface of a mastoid bone such that the docking point, the control point and the entry point are on the same straight-line path; and
an otologic drill, separate and distinct from the feeler mechanism, configured to drill a passage from the docking point up to the cochlea through the mastoid bone along the straight-line path as determined by the equation, so as to create a passage up to the cochlea, wherein the docking point for the otologic drill and the straight-line path followed by the otologic drill are predetermined by the device before drilling the passage.

13. The otologic surgery device according to claim 1, wherein the position-identification means comprises a feeler that is at a distal end of a hinged arm, each hinge of the arm provided with an angular position sensor, the hinged arm has a proximal end connected to a base movably mounted on a support to move along three axes in translation.

14. The otologic surgery device according to claim 13, wherein each axis is fitted with a corresponding position sensor configured to emit signals corresponding to a respective sensed position of a sensitive tip of the feeler.

* * * * *